United States Patent [19]

Kapitanov

[11] 4,316,469
[45] Feb. 23, 1982

[54] SURGICAL APPARATUS FOR SUTURING SOFT TISSUES WITH LENGTHS OF SUTURING MATERIAL WITH SPICULES

[76] Inventor: Nikolai N. Kapitanov, ulitsa Levchenko, 3, kv. 9, Moscow, U.S.S.R.

[21] Appl. No.: 82,634

[22] Filed: Oct. 5, 1979

Related U.S. Application Data

[63] Continuation of Ser. No. 831,259, Sep. 7, 1977, abandoned.

[30] Foreign Application Priority Data

Sep. 7, 1976 [SU] U.S.S.R. .............................. 2403384

[51] Int. Cl.³ .......................................... A61B 17/04
[52] U.S. Cl. ................. 128/334 R; 128/217; 128/330
[58] Field of Search ............. 128/42 B, 42 E, 92 EC, 128/217, 329–330, 334–340

[56] References Cited

U.S. PATENT DOCUMENTS

| | | | |
|---|---|---|---|
| 3,016,895 | 1/1962 | Sein | 128/217 |
| 3,699,969 | 10/1972 | Allen | 128/330 |
| 3,716,058 | 2/1973 | Tanner | 128/337 |
| 3,820,545 | 6/1974 | Jefferts | 128/330 |
| 4,006,747 | 2/1977 | Kronenthal et al. | 128/337 |

*Primary Examiner*—Dalton L. Truluck
*Attorney, Agent, or Firm*—McAulay, Fields, Fisher, Goldstein & Nissen

[57] ABSTRACT

A surgical apparatus for suturing soft tissues with lengths of suturing material with spicules comprises at least one hollow needle, mounted in the apparatus body, with a bore to accommodate a length of suturing material, introduced into the tissue to be sutured together with the needle, as well as a stop situated inside the needle bore. The needle in adapted to move longitudinally over the stop so as to retain the length of suturing material in the tissue being sutured while the needle is being withdrawn therefrom, and provided with an actuator to impart the longitudinal movement thereto.

8 Claims, 18 Drawing Figures

SURGICAL APPARATUS FOR SUTURING SOFT TISSUES WITH LENGTHS OF SUTURING MATERIAL WITH SPICULES

This is a continuation of application Ser. No. 831,259 filed Sept. 7, 1977, now abandoned.

BACKGROUND OF THE INVENTION

The present invention relates to medical equipment, and more particularly to surgical apparatus for suturing soft tissues; it can be advantageously used for suturing organs with thick walls, for example, the walls of the left ventricle of the heart, or the liver, with lengths of a suturing material with spicules made of metal or of a resorptive material.

Known in the art is the use of special wires with spicules for the suturing of tendons. Such wires have a round or triangular cross-section, or are band-shaped. The spicules may be directed either unilaterally, so as to provide for the withdrawal of the wire upon the adhesion of the sutured tissues, or multilaterally, in which case the spicules must be made of a resorptive material.

The suturing of tissues with wire having spicules is performed manually. ATRAUMATIC needles (Registered Trademark) are attached to the ends of lengths of the wire and the needles are inserted, during suturing, into the end faces of the incised tendon.

Then, the needles with the ends of the wire secured therein are brought out through the tendon and the surrounding tissue onto the surface of the patient's body, where they are secured by means of a perforated washer, whereupon the needles are removed.

After a period of time necessary for the adhesion of the tendons, the wire is withdrawn.

The necessity of securing the ends of the wire with spicules on the surface of the body prevents the use of such wires for suturing tissues of internal organs.

Besides, prior art wires cannot be used for suturing organs with thick walls, since the suture effected with the wire passes close to the surface of the organ, which results in the formation of a pocket within the wound and, subsequently, retards regeneration of the tissues.

The necessity of suturing the tissues with wire by hand prolongs the time of surgery.

SUMMARY OF INVENTION

It is an object of the invention to provide a surgical apparatus ensuring the suturing of soft tissues with lengths of suturing material with spicules.

Another object of the invention is to provide for the reliable suturing of soft tissues of any thickness throughout the depth of the incision.

The invention resides in a surgical apparatus for suturing soft tissues with lengths of suturing material with spicules, which comprises, according to the invention, at least one hollow needle with a bore, mounted in the body of the apparatus, said bore being intended for accommodating said length of suturing material, that is introduced together with the needle into the tissue to be sutured, and a stop stationary in relation to the body, situated within the bore of the needle, with the needle being secured in the body movably longitudinally over the stop, enabling the length of suturing material to be retained in the tissue being sutured while the needle is being withdrawn, and is provided with an actuator for imparting said movement thereto.

Such an embodiment of the apparatus provides for rapid and reliable suturing of tissue all the way through an incision by applying sutures with lengths of suturing material with spicules, which improves the contact of the dissected tissues being sutured and speeds up the regeneration of tissues in the plane of the dissection.

Besides, the use of hollow needles allows suturing to be carried out with resorptive suturing material made for example, of biological polymers.

The apparatus may be used both for the suturing of the walls of internal organs, parenchymatous organs, and for suturing the edges of flesh wounds. The apparatus provides wide scope for maneuvering when applying sutures.

It is advisable that the apparatus comprise a group of said needles with stops, arranged in parallel, and that the actuator for moving the needles in relation to the stops be common for the entire group.

This ensures uniform arrangement of the sutures in the tissue being sutured and speeds up suturing in case of incisions of great extension, owing to the application of a group of sutures simultaneously.

A preferable embodiment of the actuator moving the needles in relation to the stops appears as a slide with through holes in which the rear ends of the needles are secured, and a rod, one of its ends being attached to said slide and the other bearing a handle.

Such an embodiment of the actuator provides for skew-free movement of the needles.

It is desirable that the apparatus be provided with a detent for the degree of protrusion of the needles with stops from the body, appearing as a plate with parallel through slots, mounted in the body with the possibility of occupying two fixed positions in the direction of movement of the needles, and also movable in each of said positions in a direction along its own slots, passing through which are the rear ends of the stops and the rod of the actuator, having at said point respective grooves, the groove for the rod having an expanded portion corresponding to the full cross-section of the rod and providing, in a definite position of the plate, for the movement by the actuator of the needles relative to the stops.

This ensures reliable piercing by each needle of the edges of the wound to different depths.

In order to ensure the setting of the plate in the aforementioned fixed positions, it is advisable to mount on the body two leaf springs, deflectable in opposite directions, and having two slots facing each other, which serve as guides ensuring the movement of the plate.

This provides for reliable operation of the detent of the degree of protrusion of the needles with stops and for its convenient handling.

A preferred embodiment of the apparatus is for the latter to be made of two detachable halves, each of which is embodied in accordance with one of the aforementioned apparatus and which are provided with a means for rigid detached fixation of one half in relation to the other half of the apparatus in such a position whereby the needles of one half cross at an angle to the needles of the other half of the apparatus, so as to secure, in the process of suturing, the counter passage of the needles through both edges of the tissue being sutured, at appropriate angles.

Such an embodiment of the apparatus provides for the approximation of the edges of wounds by the apparatus itself and subsequent suturing thereof.

The invention will now be described in greater detail with reference to preferred embodiments thereof, taken in conjunction with the accompanying drawings, wherein:

DESCRIPTION OF INVENTION

A surgical apparatus for suturing soft tissues with lengths of suturing material with spicules comprises a body 1 (FIGS. 1 and 2) with a hollow needle 2 mounted therein, which has a bore 3 intended for accommodating a length 4 (FIG. 1) of suturing material with spicules 5. Situated in the bore 3 of the needle 2 is a stop 6, serving for the movement of the needle 2 thereover and retaining the length 4 of suturing material within the tissue being sutured.

Figure 1:
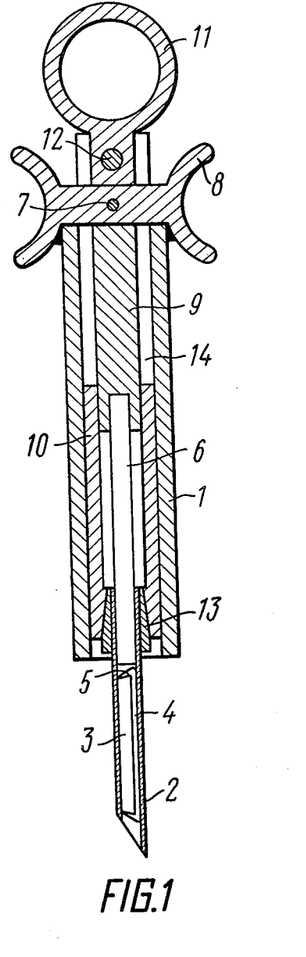
FIG. 1 is a longitudinal section view of a surgical apparatus with one needle for suturing soft tissues with lengths of suturing material having spicules, according to the invention.
Figure 2:
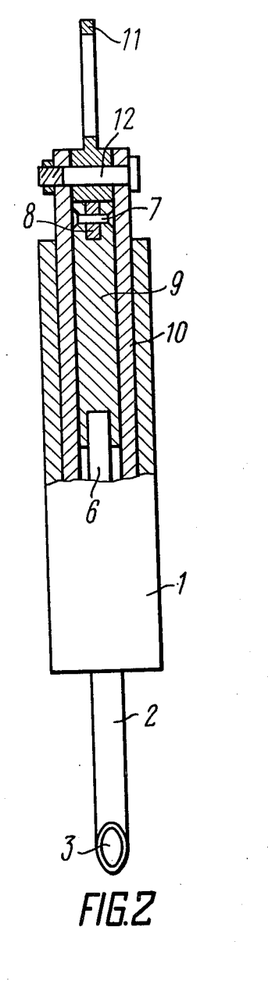
FIG. 2 is a partially cut lateral view of the apparatus.

The body 1 is rigidly connected by means of a pin 7 with a yoke 8 and a rod 9, in which the stop 6 is secured.

The needle 2 has an actuator for longitudinal movement over the stop 6, formed by a cylindrical brace 10 passing within the body 1, and embracing on the outside the rod 9 with the stop 6 and provided at one end with a handle 11 which is fastened to the brace 10 by means of a pin 12. At its other end the brace 10 has a conical socket interacting with a conical bush 13, serving for the detachable mounting of the needle 2 on the end of the brace 10.

The brace 10 has longitudinal slots 14 for the passage of the yoke 8.

Figures 3, 4, 5, 6:
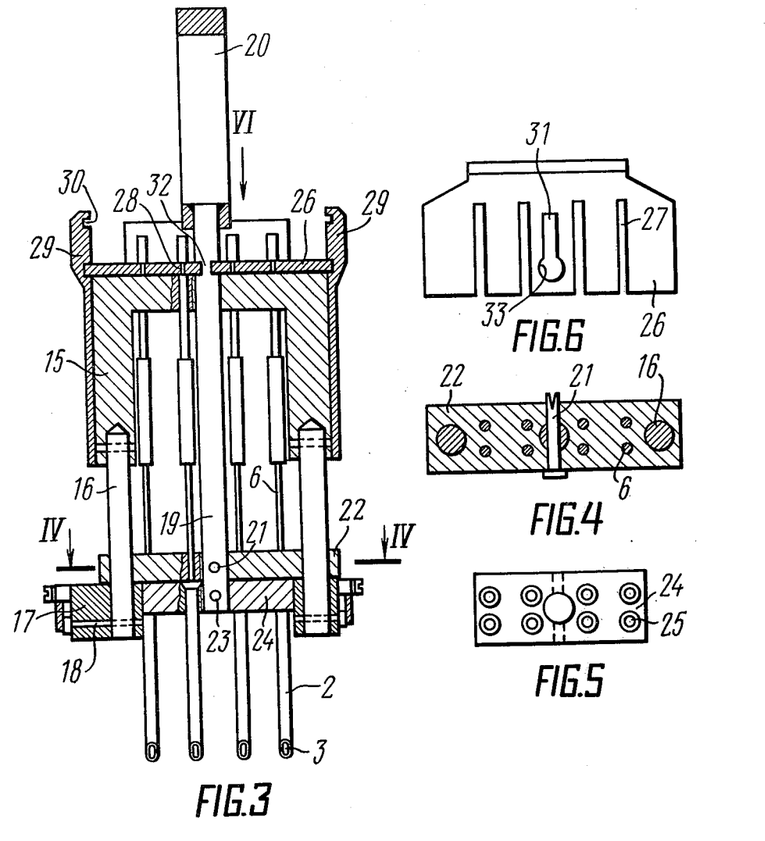
FIG. 3 is a longitudinal section view of a surgical apparatus for suturing soft tissues with lengths of suturing material having spicules, with a group of needles, according to the invention.
FIG. 4 is a section view taken line IV—IV of FIG. 3.
FIG. 5 is a top view of the attachment to the actuator of the apparatus shown in FIG. 3.
FIG. 6 is a view along arrow 6 of FIG. 3 of the plate of the detent of the degree of protrusion of the needles and stops from the body of the apparatus.

The apparatus may contain a group of needles 2 with stops 6 arranged in parallel and having a common actuator intended for the simultaneous movement of the needles 2 relative to the stops 6. This apparatus has a body shaped like a yoke 15 (FIG. 3), rigidly connected with rods 16, which, in turn, are fastened with a bracket 17 by means of pins 18. The actuator, serving to move the hollow needles 2 relative to the stops 6, is formed by a brace 19 which has a handle 20 at one end and connected through a pin 21 (FIGS. 3 and 4) with a plate 22 and by a pin 23 (FIG. 3) with an attachment 24 (FIGS. 3 and 5). The plate 22 and attachment 24 form the slide of the actuator. Made in the attachment 24 are through holes 25 (FIG. 5), in which the rear ends of the needles 2 (FIG. 3) are fastened.

The front end of each of the stops 6 enters the plate 22 and the bores 3 of the needles 2.

The apparatus is provided with a detent of the degree protrusion of the needle 2 and stop 6 out of the bracket 17 of the body, representing a plate 26 with a bent edge for retaining it and with parallel through slots 27 (FIG. 6), passing through which are the rear ends of the stops 6 (FIG. 3), having grooves 28 (FIG. 3) corresponding to the slots 27 (FIG. 6). The plate 26 is set on the yoke 15 of the body so that it can take two fixed positions in the direction of a movement of the needles 2, and also movably in each of said positions in a direction along its own slots 27 (FIG. 6). In order to secure the setting of the plate 26 in said fixed positions mounted on the yoke 15 (FIGS. 3 and 7) are two leaf springs 29 deflectable in opposite directions with two slots 30 facing each other, serving as guides for ensuring said movements of the plate 26. The plate 26 has also a slot 31 (FIG. 6) for the passage therethrough of the rod 19 (FIG. 3) which has a bore 32 corresponding to the slot 31 (FIG. 6). The slot 31 has an expanded portion 33 corresponding to the full diameter of the rod 19 (FIG. 3) and providing, with the plate 26 in a definite position, for the longitudinal movement of rod 19 and for operation of the actuator moving the needles 2 relative to the stops 6.

A surgical apparatus for suturing soft tissues may consist of two halves, each having an embodiment as described above and comprising either one needle 2, as the apparatus represented in FIG. 1, or a group of needles 2, as the apparatus represented in FIG. 3.

Each half of the apparatus must be provided with means for the mutual rigid detachable fixation of said halves in a position whereby the needles 2 of one half cross at an angle to the needles 2 of the other half of the apparatus, so as to secure in the process of suturing the counter passage of the needles 2 through both edges of the tissue being sutured, at appropriate angles.

Figure 8:
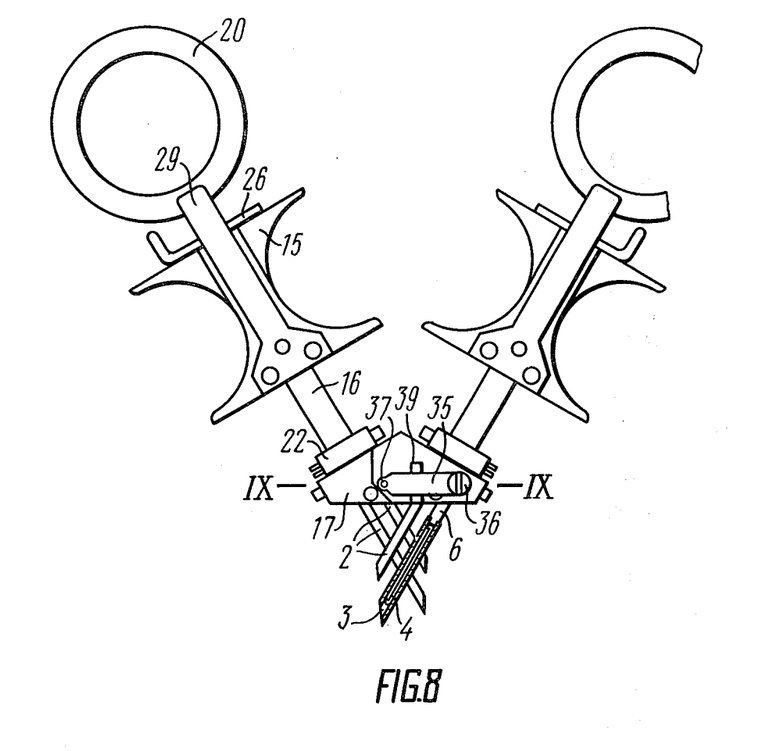
FIG. 8 is a view of a surgical apparatus for suturing soft tissues with lengths of suturing material having spicules, comprising two halves, each of which has a group of needles, according to the invention.
Figure 9:
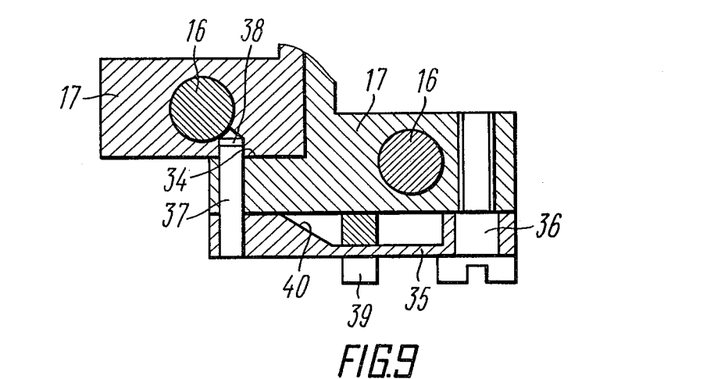
FIG. 9 is a section view taken along line IX—IX of FIG. 8.
Figure 10:
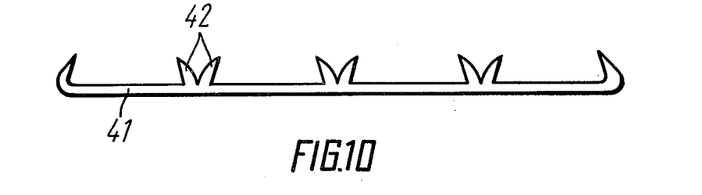
FIG. 10 shows a variant of a length of suturing material with spicules, as is used in apparatus embodied according to the invention.

An apparatus comprising two halves, each having an embodiment as the apparatus represented in FIG. 3, is represented in FIG. 8. The means for rigid detachable fixation of the halves of the apparatus comprise a slot 34 (FIG. 9) made in the bracket 17 of one half, which engages with the bracket 17 of the other half, and a leaf spring 35, fastened with a screw 36 to one of the brackets 17 and having a pin 37 which enters a hole 38 of the other bracket 17. In order to withdraw the pin 37 from the hole 38 and dissasemble the apparatus, a slide 39 is mounted under the spring 35 which interacts with a bevel 40 on the spring 35. Prior to suturing, lengths 4 of suturing material (FIG. 1), having two spicules 5 each, or lengths 41 of suturing material (FIG. 10), having several spicules 42 each, are placed in the hollow needles 3 (FIGS. 1, 3 and 8).

The operation of the surgical apparatus for suturing soft tissues with lengths of suturing material with spicules, is as follows.

An apparatus with one needle 2 (FIG. 1), as represented in the drawing, is prepared for operation.

Figure 11:
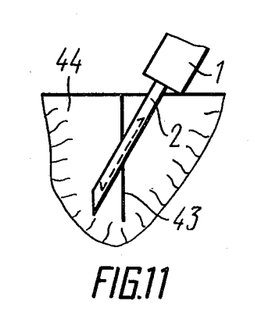
FIG. 11 is a diagrammatic representation of the suturing of soft tissues by means of an apparatus with one needle, according to the invention.
Figure 12:
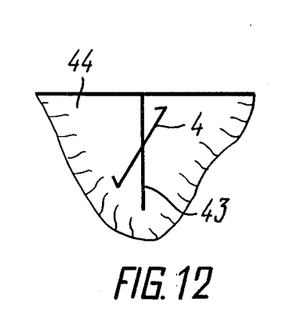
FIG. 12 shows a suture produced by suturing soft tissues by means of a surgical apparatus having one needle, according to the invention.

The needle 2 of the apparatus, is held by the surgeon by the handle 11 (FIG. 1) and yoke 8, is introduced into the approximated edges of the wound 43 (FIG. 11) of the soft tissue 44. The needle is so introduced as to pass through both edges of the wound 43 (FIG. 11) of the soft tissue 44. Then, seeing to it that the body 1 of the apparatus is not drawn away from the surface of the tissue 44 being sutured, the surgeon pulls handle 11 (FIG. 1) upward, thereby moving the needle 2 over the stop 6 (FIG. 1) and withdrawing it from the tissue 44 (FIG. 11). As this takes place, the stop 6 (FIG. 1) and the length 4 of suturing material remain in the tissue 44 (FIG. 12), joining the edges of the wound 43. Thereupon, the apparatus is removed from the newly formed suture. For the placement of a next suture, the needle 2 (FIG. 1) with the bush 13 is taken off the brace 10 and stop 6 to be charged with another length 4 of suturing material, the needle 2 is connected with the apparatus, and the wound is sutured with the next length 4 of suturing material.

Figure 13:
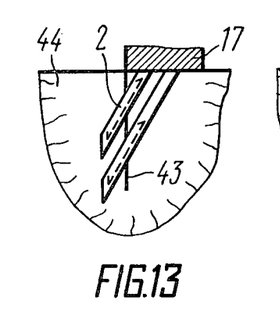
FIG. 13 is a diagrammatical representation of the suturing of soft tissues by means of a surgical apparatus having a group of needles, according to the invention.
Figure 14:
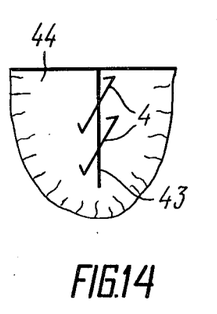
FIG. 14 is a view of a suture produced by suturing soft tissues by means of a surgical apparatus having a group of needles, according to the invention.

For suturing wounds of great extension and depth, an apparatus is used as represented in FIG. 3 and having a group of needles 2. The needles 2 are introduced into the approximated edges of the wound 43 (FIG. 13) so that they pass through the soft tissues 44 of the edges of the wound 43, while the bracket 17 of the apparatus rests on the surface of the tissue 44. Then, taking care not to remove the bracket 17 from the surface of the tissue 44 being sutured, the handle 20 (FIG. 3) is drawn upwards, thereby moving the needles 2 over the stops 6 and with drawing them from the tissue 44 (FIG. 14). As this takes place, the lengths 4 of suturing material, held by the stops 6 (FIG. 3), remain motionless and the edges of the wound 43 (FIG. 14), upon the removal of the apparatus, are sutured with the lengths 4 of suturing material.

Figure 7:
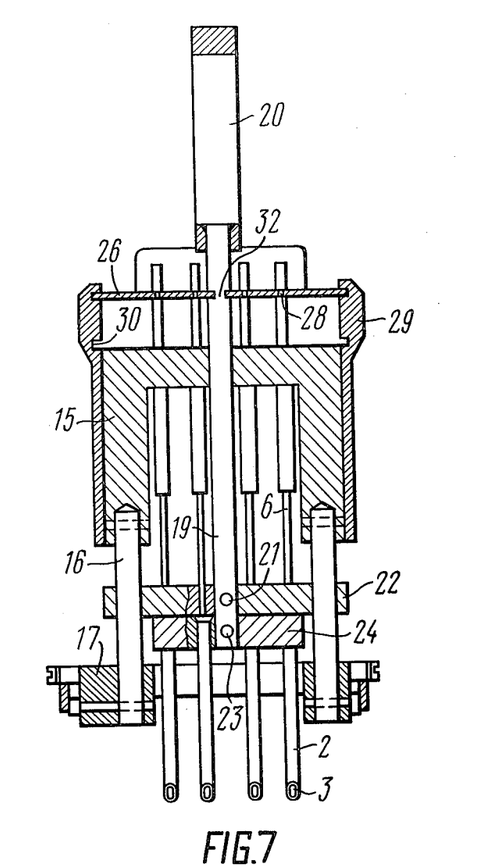
FIG. 7 is a view of the apparatus shown in FIG. 3, but with a different position of the detent of the degree of protrusion of the needles and stops from the body of the apparatus.

For the placement of a next row of sutures with the apparatus, the pin 23 (FIG. 3) must be withdrawn, and the attachment 24 must be detached and replaced with another one provided with the needles 2 charged with lengths 4 of suturing material. For regulating the degree of protrusion of the needles 2 with the stops 6 from the bracket 17 of the body of the apparatus and, therefore, of the depth of the suture, the plate 26 is set either in the lower slots 30, as shown in FIG. 3, or in the upper slots 30, as shown in FIG. 7.

The approximation of the edges of the wound can be effected by the apparatus itself. To this end, an apparatus consisting of two halves is used, as as represented in FIG. 8.

Figures 15, 16:
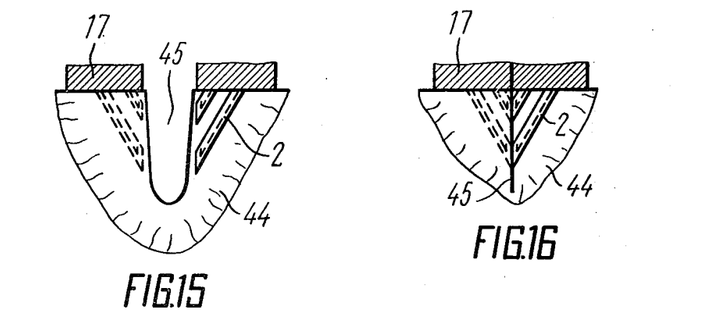
FIGS. 15, 16 and 17 are diagrammatic representations of the suturing of soft tissues by means of a surgical apparatus having two halves with groups of needles, according to the invention.

Prior to suturing, the apparatus is dismantled into its two halves, and the plate 26 is inserted into the upper slots 30 (FIG. 7), in a position corresponding to the least protrusion of the needles 2 from the bracket 17 of the body of the apparatus. The needles 2 of each of the halves are introduced into the edges of the incision 45 (FIG. 15) until the bracket 17 of the body of the apparatus comes to rest against the surface of the tissue 44. Then, both halves of the apparatus are joined and secured with the pin 37 (FIG. 8). Therewith, the edges of the incision 45 (FIG. 16) are brought together. Then, the plate 26 (FIG. 3) is reset into the lower slots 30, in a position corresponding to the greater protrusion of the needles 2 from the bracket 17 of the body of the apparatus.

In this case the plate 26 is reset from the upper slots 30 into the lower slots 30 with the plate in such a position whereby the rod 19 is embraced by the narrow portion of the slot 31 (FIG. 6), so that the rod 19 is secured relative to the plate 26 and travels together with the latter.

Figure 17:
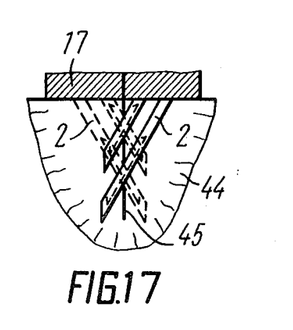

As a result, the needles 2 pierce the opposite edges of the incision 45 (FIG. 17) of the tissue 44. Then, the plate 26 (FIG. 3) is moved along the lower slots 30 into a position whereby the rod 19 passes through the expanded portion 33 (FIG. 6) of the slot 31. This position provides for operation of the actuator of the needles 2, so that the latter can be moved relative to the stops 6.

Figure 18:
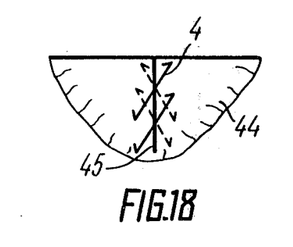
FIG. 18 shows a suture produced by suturing soft tissues by means of a surgical apparatus having two halves with groups of needles, according to the invention.

The needles 2 are withdrawn by means of the handle 20, thereby moving them relative to the stationary stops 6. As this takes place, the brackets 17 of the apparatus remain pressed against the surface of the tissue being sutured. Then, the halves of the apparatus are unlocked and removed, leaving the incision 45 sutured with a suture shown in FIG. 18.

What is claimed is:

1. A surgical apparatus for suturing soft tissues by means of pieces of a suture material with spicules, comprising: a housing being in the form of hollow rods with handle means for receiving fingers of a surgeon's hand; a set of detachable needles being movable in the longitudinal direction relative to said housing, whereby, each of said needles is provided with a through longitudinal bore for placement of said piece of the suture material therethrough and into said needle; drive means being stationary and movable relative to said needles and said housing, respectively; a stop member being mounted within said housing being stationary relative to said housing in the form of stems having a variable cross-section whereby the free ends of said stems being placed within said needles in a stopped position with said pieces of the suture material and an actuator means for imparting longitudinal movement to said needles, said actuator being defined by a slide member having holes therein whereby, said needles have their rear ends secured in the holes of the slide; said actuator being further defined by a rod, one end of which is fastened to the slide; and said handle means disposed on the other end of said rod.

2. An apparatus as claimed in claim 1, comprising: a detent having a degree of protrusion associated with said needles for co-action with stops from said body; a plate of said detent formed with parallel through slots, mounted in said body and capable of taking two positions fixed in the direction of movement of said needles, and being also movable in each of said positions in a direction along its own slots; said actuator rod, passing through one of said slots of the plate and having a bore at the place of its passage corresponding to the width of the slot and restraining the rod from longitudinal movement relative to the plate; said slot for the rod having an expanded portion corresponding to the full cross-section of the rod and providing for its longitudinal movement relative to the plate, at a definite position of the latter, and for the operation of said actuator to thereby impart movement to the needles; said stops passing through said slots in the plate being provided with grooves at the point of their passage, corresponding to the width of the slots and restraining the stops from longitudinal movement relative to said plate.

3. An apparatus as claimed in claim 2, comprising two leaf springs mounted on said body, deflectable in opposite directions and having two pairs of slots facing each other, serving to set therein plate in said fixed positions and ensuring the movement of said plate there along.

4. A surgical apparatus for suturing soft tissues with lengths of suturing material having spicules, comprising: two halves detachably connected with each other; a body of each of said halves; a needle for each of said halves mounted in said body and longitudinally movable therein, having a longitudinal bore intended to accommodate said length of suturing material, introduced together with the needle into the tissue being sutured; a stop in each of the halves, mounted in its body immovably with respect to the latter, and situated within said bore of the needle of a respective half, whereby, during longitudinal movement of the needle being withdrawn from the tissue being sutured, said length of suturing material is retained in the tissue; an actuator means for each half adapted to impart longitudinal movement to said respective needles; a means for rigid detachable fixation of one of said halves relative to the other in a position adapted to allow said needle of one half to cross the needle of the other half in the process of suturing, for the counter passage of said needles through both edges of the tissue being sutured at appropriate angles.

5. A surgical apparatus for suturing soft tissues with lengths of suturing material with spicules, comprising: two halves detachable connected to each other; a body for each half; a group of needles of each half, mounted in said body and longitudinally movable therein; each needle being defined by a longitudinal bore intended for accommodating said length of suturing material to be introduced together with the needle into the tissue to be sutured; stops mounted in said body of each half, being immovable with respect to the body and situated within said bores of the needles and providing, during said longitudinal movement of the needles being withdrawn from the tissue being sutured, for retention of said lengths of suturing material in the tissue; an actuator for each half for imparting longitudinal movement to the needles; means for rigid detachable fixation of one half to the other, in a position whereby the needles of one half cross at an angle to the needles of the other half so as to provide, in the process of suturing, counter passage of the needles through both edges of the tissue being sutured at appropriate angles.

6. An apparatus as claimed in claim 5, comprising: a slide associated with said actuator for each half having holes therein for receiving; said needles at their rear ends secured to the holes; a rod of said actuator of each half having one of its ends attached to said slide; and a handle disposed on the other end of said rod.

7. An apparatus as claimed in claim 6, comprising: a detent having a degree of protrusion associated with said needles for co-action with stops from said body of each half; a plate of said detent formed with parallel through slots, mounted in said body and capable of taking two positions fixed in the direction of movement of said needles, and being also movable in each of said positions in a direction along its own slots; said actuator rod of each half, passing through one of said slots of said plate, having a bore at the point of its passage, corresponding to the width of the slot and serving to restrain the rod from longitudinal movement relative to the plate; said slot for the rod having an expanded portion corresponding to the full cross-section of the rod and providing for longitudinal movement relative to the plate at a definite position of the latter, and for operation of said actuator, to impart movement to the needles; said stops of each half, passing through said slots of the plate of a respective half, and having bores at the point of their passage, corresponding to the width of the slots and serving to restrain the stops from longitudinal movement relative to said plate.

8. An apparatus as claimed in claim 7, comprising: two leaf springs associated with each half being mounted on the body of their respective halves and being deflectable in opposite directions, two pair of slots facing each other adapted to set said detent plate therein in said fixed positions and providing for the movement of said plate therealong.

* * * * *